US009055885B2

(12) United States Patent
Horvath et al.

(10) Patent No.: US 9,055,885 B2
(45) Date of Patent: Jun. 16, 2015

(54) WHITE COHERENT LASER LIGHT LAUNCHED INTO NANO FIBERS FOR SURGICAL ILLUMINATION

(71) Applicants: Christopher Horvath, Mission Viejo, CA (US); Michael J. Papac, North Tustin, CA (US); Laszlo Romoda, San Clemente, CA (US); Ronald T. Smith, Irvine, CA (US); Michael J. Yadlowsky, Sunnyvale, CA (US)

(72) Inventors: Christopher Horvath, Mission Viejo, CA (US); Michael J. Papac, North Tustin, CA (US); Laszlo Romoda, San Clemente, CA (US); Ronald T. Smith, Irvine, CA (US); Michael J. Yadlowsky, Sunnyvale, CA (US)

(73) Assignee: ALCON RESEARCH, LTD., Fort Worth, TX (US)

( * ) Notice: Subject to any disclaimer, the term of this patent is extended or adjusted under 35 U.S.C. 154(b) by 61 days.

(21) Appl. No.: 14/076,215

(22) Filed: Nov. 10, 2013

(65) Prior Publication Data

US 2014/0066723 A1    Mar. 6, 2014

Related U.S. Application Data

(62) Division of application No. 13/313,105, filed on Dec. 7, 2011, now abandoned.

(60) Provisional application No. 61/440,568, filed on Feb. 8, 2011.

(51) Int. Cl.
*A61B 1/07* (2006.01)
*A61B 19/00* (2006.01)
*A61F 9/008* (2006.01)

(52) U.S. Cl.
CPC . *A61B 1/07* (2013.01); *A61F 9/008* (2013.01); *A61B 19/5202* (2013.01); *A61B 2019/5206* (2013.01)

(58) Field of Classification Search
CPC ................ A61B 1/07; A61B 19/5202; A61B 2019/5206; A61F 9/008
USPC .......... 600/166, 177, 182, 249; 351/221, 243; 362/553, 572, 574; 374/43; 382/128; 604/20, 21; 606/4, 11, 15, 16, 12; 607/89, 88
See application file for complete search history.

(56) References Cited

U.S. PATENT DOCUMENTS 4,449,535 A  *  5/1984  Renault ........................ 600/312
5,062,431 A     11/1991  Potter
(Continued)

FOREIGN PATENT DOCUMENTS

EP    1114608 A1    7/2001
JP    10286235 H    10/1998
(Continued)

OTHER PUBLICATIONS

Valerie J. Nadeau, et al., Laser-Pumped Endoscopic Illumination Source, 2059-62, Aug. 20-24, 2008, 30th Annual International IEE EMBS Conference.
(Continued)

*Primary Examiner* — Pedro Philogene
(74) *Attorney, Agent, or Firm* — Jason Finch

(57) ABSTRACT

Disclosed is an exemplary surgical illumination system that includes a first laser configured to emit a first light beam having a first spectral range, and an illumination probe optically connectable to the first laser. The first laser may be configured as a supercontinuum laser. The surgical illumination system may include a second laser configured to emit a second light beam having a second spectral range, and a beam combiner for combing the first and second laser beams to form a third laser beam having a spectral range of the first and second lasers. The illumination probe includes a fiber optic cable for delivering at least a portion of the first light beam to a surgical site. The fiber optic cable includes a fiber optic core having a diameter of 100 microns or less.

16 Claims, 5 Drawing Sheets

(56) References Cited

U.S. PATENT DOCUMENTS

| | | | |
|---|---|---|---|
| 6,183,086 | B1 | 2/2001 | Neubert |
| 6,445,939 | B1 | 9/2002 | Swanson et al. |
| 6,485,413 | B1 | 11/2002 | Boppart et al. |
| 6,813,050 | B2 | 11/2004 | Chen et al. |
| 7,143,769 | B2 * | 12/2006 | Stoltz et al. .............. 128/898 |
| 7,261,687 | B2 | 8/2007 | Yang |
| 7,364,543 | B2 | 4/2008 | Yang et al. |
| 7,433,046 | B2 | 10/2008 | Everett et al. |
| 7,783,346 | B2 * | 8/2010 | Smith et al. .............. 604/21 |
| 7,980,745 | B2 | 7/2011 | Shanbaky |
| 2005/0259314 | A1 | 11/2005 | Tokuhisa et al. |
| 2008/0246920 | A1 | 10/2008 | Buczek |
| 2009/0054957 | A1 * | 2/2009 | Shanbaky .............. 607/89 |
| 2009/0143772 | A1 | 6/2009 | Kurtz |
| 2010/0056928 | A1 | 3/2010 | Zuzak et al. |
| 2010/0182569 | A1 | 7/2010 | Artsyukhovich et al. |
| 2010/0228238 | A1 | 9/2010 | Brennan et al. |
| 2010/0318074 | A1 * | 12/2010 | Dacquay et al. .............. 606/4 |

FOREIGN PATENT DOCUMENTS

| | | |
|---|---|---|
| JP | 2009519766 T2 | 5/2009 |
| JP | 2010178787 A2 | 8/2010 |
| WO | 03077746 A2 | 9/2003 |
| WO | 2009094451 A2 | 7/2009 |

OTHER PUBLICATIONS

YAQOOB, Z. et al, "Methods and application areas of endoscopic optical coherence tomography", J. Biomed. Opt., 11 (6), 063011, pp. 1-19, (2006).

Aguirre, A.D., et al., "Continuum generation in a novel photonic crystal fiber for ultrahigh resolution optical coherence tomography at 800 nm and 1300 nm," Opt. Express, Feb. 6, 2006, 1145-60, 14:3.

Sacchet, D., et al, "Simultaneous dual-band ultra-high resolution full-field optical coherence tomography," Opt. Express, Nov. 24, 2008, 19434-446, 16:24.

Spoler, F., et al, "Simultaneous dual-band ultra-high resolution optical coherence tomography," Opt. Express, Aug. 20, 2007, 10832-841, 15:17.

Pan, Y., et al, "Nonivasive Imaging of Living Human Skin With Dual-Wavelength Optical Coherence Tomography in Two and Three Dimensions," J. Biomed. Opt., Oct. 1998, 446-455, 3:4.

Gelikonov, V.M., et al, "Two-Wavelength Optical Coherence Tomography," Radiophys. & Quantum Electron., 2004, 848-859, 47:10-11.

"Fiberoptic Illuminator (FI)," 510(k) Summary K062259 Premarket Notification, iScience Surg. Corp., May 3, 2006, 5 pages.

Xue, et al., "Ultrahigh resolution optical coherence tomography with femtosecond Ti:sapphire laser and photonic crystal fiber", Chin Sci Bull., Jul. 2008, 1:53(13), 1963-66.

* cited by examiner

WHITE COHERENT LASER LIGHT LAUNCHED INTO NANO FIBERS FOR SURGICAL ILLUMINATION

RELATED APPLICATION

The present application is a divisional of and claims benefit of U.S. patent application Ser. No. 13/313,105 filed 7 Dec. 2011, titled "WHITE COHERENT LASER LIGHT LAUNCHED INTO NANO FIBERS FOR SURGICAL ILLUMINATION," the text of which is specifically incorporated by reference herein.

This application claims priority to U.S. Provisional Application Ser. No. 61/440,568 filed on Feb. 8, 2011, the contents of which are incorporated herein by reference.

BACKGROUND

Anatomically, an eye may be divided into two distinct parts—an anterior segment and a posterior segment. The anterior segment includes a lens and extends from an outermost layer of the cornea (the corneal endothelium) to a posterior of a lens capsule. The posterior segment includes a portion of the eye behind the lens capsule. The posterior segment extends from an anterior hyaloid face (part of a vitreous body) to a retina, with which the posterior hyaloid face is in direct contact. The posterior segment is much larger than the anterior segment.

The posterior segment includes the vitreous body—a clear, colorless, gel-like substance. It makes up approximately two-thirds of the eye's volume, giving it form and shape before birth. The vitreous body is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free flowing like the aqueous humor and has normal anatomic attachment sites. One of these sites is the vitreous base, which is an approximately 3-4 mm wide band that overlies the ora serrata. The optic nerve head, macula lutes, and vascular arcade are also sites of attachment. The vitreous body's major functions are to hold the retina in place, maintain the integrity and shape of the globe, absorb shock due to movement, and to give support for the lens posteriorly. In contrast to the aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at pars plana. The surgeon inserts microsurgical instruments through the incisions, such as a fiber optic light source, to illuminate inside the eye; an infusion line to maintain the eye's shape during surgery; and instruments to cut and remove the vitreous body. A separate incision may be provided for each microsurgical instrument when using multiple instruments simultaneously.

During such surgical procedures, proper illumination of the inside of the eye is important. Typically, a thin optical fiber is inserted into the eye to provide the illumination. A light source, such as a halogen tungsten lamp or high pressure arc lamp (metal-halides, Xe), may be used to produce the light carried by the optical fiber into the eye. The light passes through several optical elements (typically lenses, mirrors, and attenuators) and is transmitted to the optical fiber that carries the light into the eye.

As with most surgical procedures, there is a benefit to minimizing the number and size of incisions required to perform the vitreo-retinal procedure. Incisions are typically only made large enough to accommodate the size of the microsurgical instrument being inserted into the interior of the eye. Efforts to minimize the incision size generally involve reducing the size of the microsurgical instrument. Reducing the number of incisions may be accomplished by integrating various microsurgical instruments. For example, the optical fiber may be incorporated into the working end of a microsurgical instrument. This may eliminate the need for a separate illumination incision and offers the advantage of directing the light beam together with the microsurgical instrument onto the target site through a common opening in the sclera. Unfortunately, at least some prior attempts at integrating multiple microsurgical instruments resulted larger instruments requiring larger incisions for insertion into the interior region of the eye, or were accompanied by a corresponding decrease in performance of one or both of the integrated surgical instruments.

DETAILED DESCRIPTION

Figure 1:
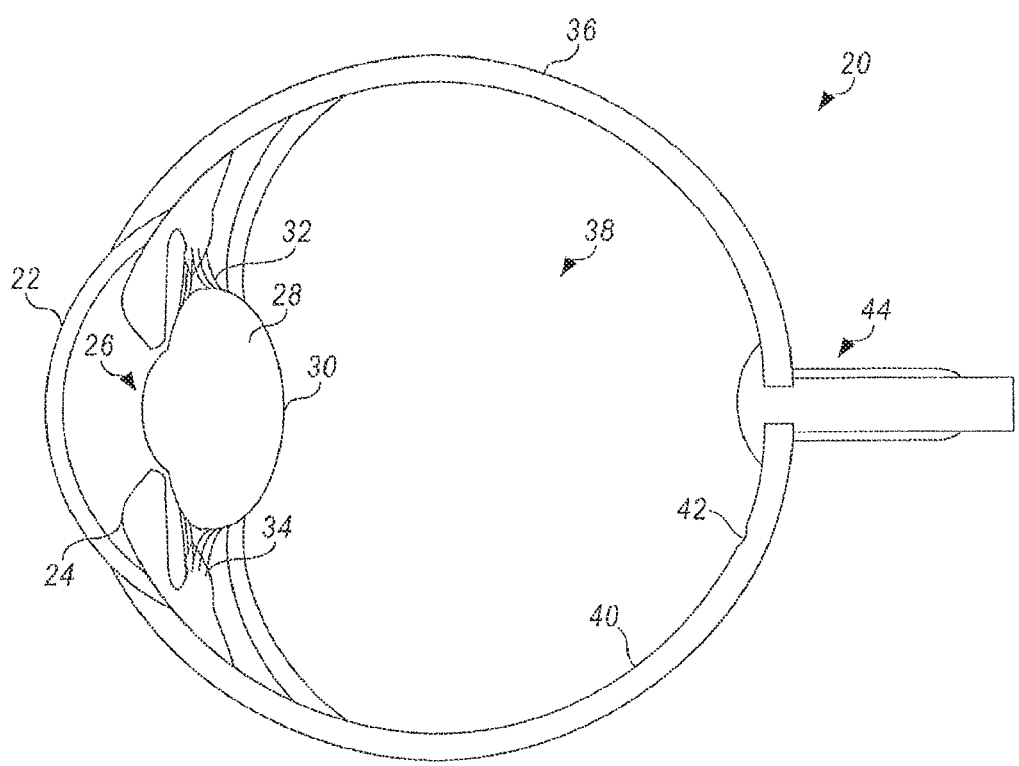
FIG. 1 is a cross-sectional view of an eye illustrating an internal anatomy of the eye.

Referring now to the discussion that follows and the drawings, illustrative approaches to the disclosed systems and methods are described in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive, otherwise limit, or restrict the claims to the precise forms and configurations shown in the drawings and disclosed in the following detailed description.

FIG. 1 illustrates an anatomy of an eye 20, which includes a cornea 22, an iris 24, a pupil 26, a lens 28, a lens capsule 30, zonules 32, ciliary body 34, sclera 36, vitreous region 38, retina 40, macula 42, and optic nerve 44. Cornea 22 is a clear, dome shaped structure on the surface of eye 20 that acts as a window, letting light into the eye. Iris 24, which corresponds to the colored part of the eye, is a muscle surrounding pupil 26 that relaxes and contracts to control the amount of light entering eye 20. Pupil 26 is a round, central opening in iris 24. Lens 28 is a structure inside eye 20 that helps focus light on retina 40. Lens capsule 30 is an elastic bag that encapsulates lens 30, helping to control the shape of lens 28 as the eye focuses on objects at different distances. Zonules 32 are slender ligaments that attach lens capsule 30 to the inside of eye 20, holding lens 28 in place. Ciliary body 34 is a muscular area attached to lens 28 that contracts and relaxes to control the size of the lens for focusing. Sclera 36 is a tough, outermost layer of eye 20 that maintains the shape of the eye. Vitreous region 38 is a large, gel-filled section located towards a back of eye 20 that helps maintain the curvature of the eye. Retina 40 is a light-sensitive nerve layer at the back of eye 20 that receives light and converts it into signals to send to the brain. Macula 42 is an area in the back of eye 20 that includes receptors for detecting fine detail in a viewed image. Optic nerve 44 transmits signals from eye 20 to the brain.

Figure 2:
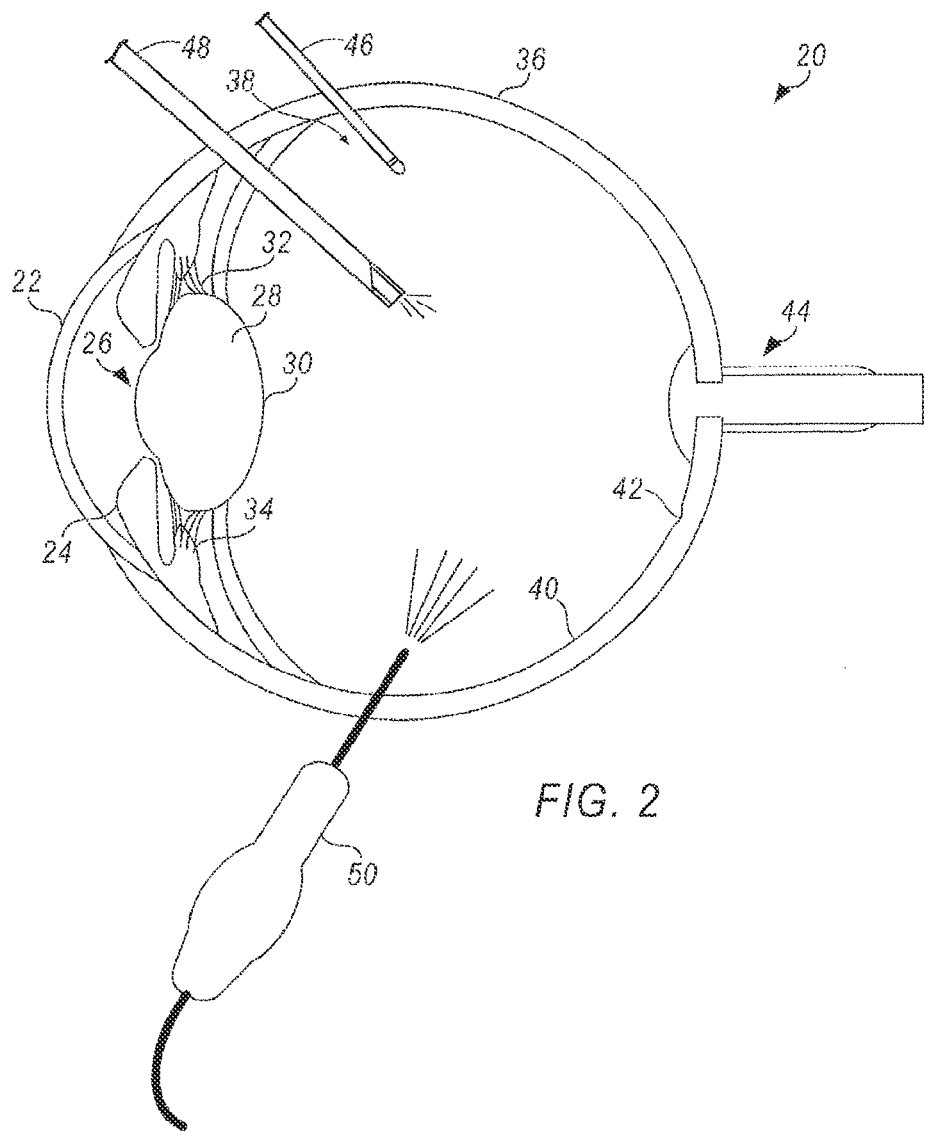
FIG. 2 is schematic illustration of an exemplary illumination probe shown illuminating an interior region of the eye of FIG. 1.

With reference to FIG. 2, various microsurgical instruments may be inserted through sclera 36 (generally at the pars plana) into vitreous region 38 in connection with performing a vitreo-retinal procedure. These may include, but are not limited to, a vitrectomy probe 40, an infusion cannula 48, and an illumination probe 50 for illuminating an interior of eye 20. Illumination probe 50 may include a fiber optic cable 52 for transferring light from a light source to illuminate the inside of vitreous region 38 of eye 20 during various intra-operative procedures, such as vitreo-retinal surgery.

Figure 3:
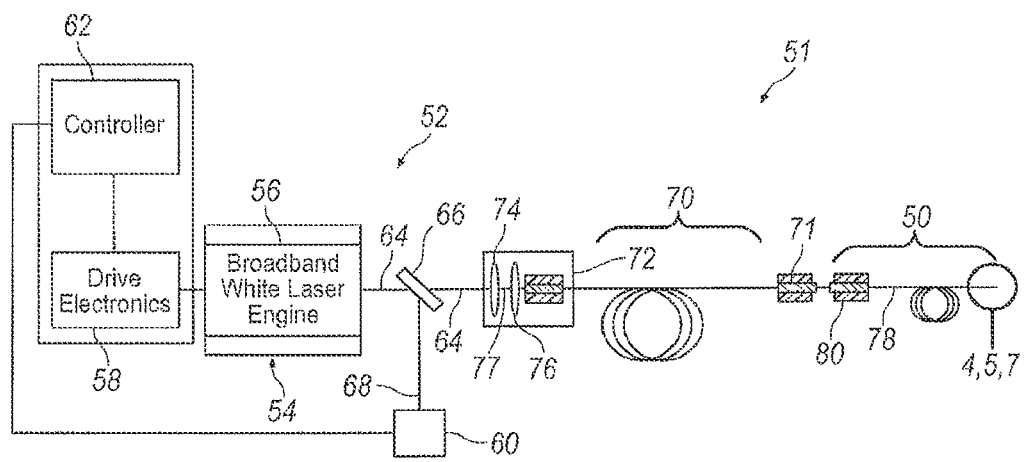
FIG. 3 is a schematic illustration of an exemplary intraocular illumination system employing a generally broadband laser light source that may be selectively optically connected to the illumination probe.

With reference to FIG. 3, an exemplary endoilluminator 51 may include an illuminator 52 and illumination probe 50. Illuminator 52 may include a light engine 54 for generating light at a particular luminous flux and chromaticity. Light produced by illuminator 52 may be transmitted to the interior region of the eye through illumination probe 50. Light engine 54 may employ a laser 56 for generating the light. Various types and configurations of lasers may be employed, including but not limited to, gas lasers, dye lasers, metal vapor lasers, solid state lasers, semiconductor lasers, fiber lasers, and supercontinuum lasers. The light may be emitted from laser 56 over a relatively wide or narrow spectral range depending on the type of laser employed. Lasers are generally capable of producing light having a relatively high degree of spatial coherence, as compared to other light sources, such as LEDs and lamp based illuminators. High spatial coherence enables the emitted light to be focused to smaller spot sizes for efficient transmission to fiber optic cables. The ability to focus the emitted light to small spot sizes may enable the use of small optic fibers, such as nano-scaled optic fibers, which may in turn allow for smaller surgical incisions for inserting illumination probe 50 into eye 20. As is the case with many surgical procedures, including vitreo-retinal procedures, it is generally desirable to limit surgical incisions to as small a size as possible. Smaller optic fibers generally require smaller surgical incisions for insertion into the eye. Depending on the size of the optic fiber employed, the incision may be small enough to render the resulting wound substantially self-healing, thereby eliminating the need to employ additional procedures to close the incision, such as sutures.

Laser 56 may be configured to produce a generally broadband white light for illuminating the interior region of eye 20. For example, laser 56 may be configured as a supercontinuum laser capable of producing a generally broadband light over a relatively wide spectral range. Supercontinuum lasers operate, for example, by passing a generally narrow bandwidth pulsed pump beam through a dispersive, non-linear medium, such as a photonic crystal fiber. As the pump beam propagates through the dispersive, non-linear medium, a series of non-linear processes act upon the pump beam to cause spectral broadening of the initial pump beam. The result is a spectral continuum extending over at least a portion of the visible spectrum. Laser 56 may also be configured to emit light covering the entire visible spectrum and extending into portions of the invisible spectrum.

Continuing to refer to FIG. 3, illuminator 52 may include various devices for controlling and monitoring the operation of laser 56, including but not limited to, drive electronics 58, power monitor 60, and controller 62. Power monitor 60 may be configured to monitor the power of a light beam 64 emitted from laser 56. A beam splitter 66, or another suitable optical device, may be used to direct a portion 68 of light beam 64 to power monitor 60. Power monitor 60 may be configured to generate an electronic signal indicative of the power of the light emitted from laser 56. Power monitor 60 may be electronically connected, either wired or wirelessly, to controller 62.

Controller 62 may at least partly control the operation of drive electronics 58. Various informational inputs may be received by controller 62, including but not limited to, various user inputs and the power signal transmitted from power monitor 60, and then heuristics, i.e., logical rules or processes, may be applied to the inputs. Outputs may then be generated that influence operation of drive electronics 58 in the context of the overall operation of illuminator 52.

In certain illumination applications, such as when employing a supercontinuum laser, it may be beneficial to further stretch the beam pulses emitted from laser 56 in the time domain. This may be accomplished by arranging a dispersive element 70 in the optical path downstream of the dispersive, non-linear medium used to generate the generally broadband white light emitted from laser 56. Dispersive element 70 may be configured as a length of dispersive optic fiber. Dispersive element 70 may include an optical coupler 71 for selectively optically coupling illumination probe 50 to illuminator 52. Alternatively, dispersive element may be integrated as part of illumination probe 50.

Continuing to refer to FIG. 3, illuminator 52 may include an optical coupler 72 for capturing and focusing light beam 64 emitted from laser 56, and focusing the light for delivery to dispersive element 70. Optical coupler 72 may include various optical elements, such as, for example, a collimating lens 74 for receiving the generally divergent light beam 64 emitted from laser 56, and a condensing lens 76 arranged optically downstream of collimating lens 74. Collimating lens 74 receives light beam 64 emitted from laser 56, and refracts the light to form a generally collimated light beam 77. Collimated light beam 77 passes through condensing lens 76, which operates to focus the collimated light beam for delivery to dispersive element 70. Optical coupler 72 may alternatively employ a ball lens for optically coupling laser 56 to dispersive element 70. These are just two examples of the various optical coupling systems that may be employed to optically couple laser 56 to fiber optic cable 52. Other optical coupling systems may also be utilized.

With continued reference to FIG. 3, illumination probe 50 may include a fiber optic cable 78 for transmitting light emitted from laser 56 to the interior of eye 20. Fiber optic cable 78 may include a fiber optic connector 80 for optically connecting fiber optic cable 78 to dispersive element 70. Fiber optic connector 80 releasably connects to correspondingly configured optical coupler 71 operably associated with illuminator 52. Optical connectors 71 and 80 enable fiber optic cable 78 to be selectively attached and detached from illuminator 52. In the exemplary configuration of endoilluminator 51 illustrated in FIG. 3, fiber optic cable 78 is shown directly connected to dispersive element 70. In practice, various additional optical elements may be disposed in the optical path between illuminator 52 and fiber optic cable 78. For example, illuminator 52 may be housed within a surgical console. An optical connector, configured similar to optical coupler 71, may be arranged in a readily accessible location on the surgical console to provide access for optically connecting fiber optic cable 78 to the connector. A series of optical elements, such as an additional length of optical fiber (which may be permanent or disposable), may be employed to optically connect illuminator 52 to the optical connector arranged on the outside of the surgical console. Other optical elements may also be employed for optically connecting fiber optic cable 78 to illuminator 52.

Figure 4:
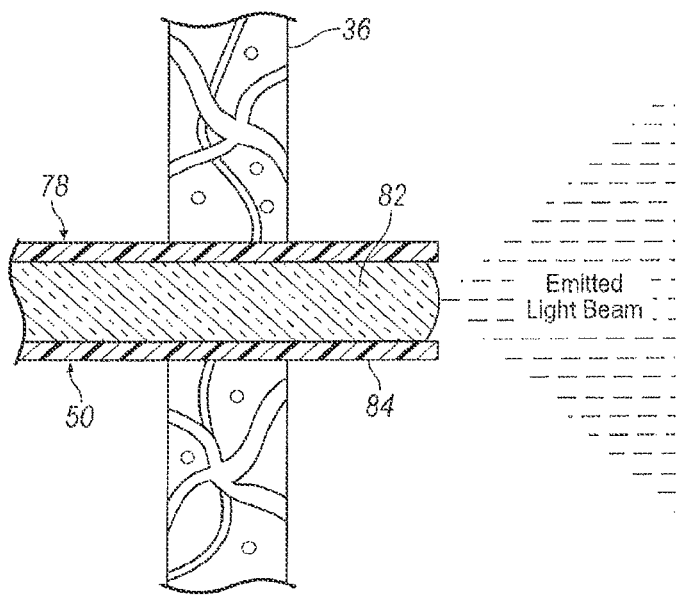
FIG. 4 is a schematic partial cross-sectional view of an end of the illumination probe shown projecting through an incision in a sclera of the eye.

Referring also to FIG. 4, fiber optic cable 78 may have any of a variety of configurations. Fiber optic cable 78 may include a flexible configuration to allow generally unimpeded manipulation of illumination probe 50. Fiber optic cable 78 may include an optically transmissive fiber optic core 82 surrounded by a cladding material 84 having a generally low index of refraction relative to fiber optic core 82. Fiber optic core 82 may be made of various materials, including but not limited to, glass and plastics. Fiber optic cable 78 may also include additional layers depending on the requirements of a particular application. For example, fiber optic cable 78 may include a buffer material encasing cladding material 84, as well as an outer protective jacket (such as a plastic or metal tube) for shielding the cable's interior components from damage.

When employing a supercontinuum laser as laser 56, the emitted light beam 64 generally possesses a high degree of spatial coherence. High spatial coherence typically enables the beam to be focused to small spot sizes for delivery to fiber optic cabling. The ability to focus light emitted from a supercontinuum laser to small spot sizes may enable the use of nano-scale optic fibers for transmitting the light emitted from laser 56 to the interior of eye 20. Nano-scale optic fibers generally have a diameter (or other largest cross-sectional dimension) of less than 100 microns. When employed as fiber optic core 82 of illumination probe 50, the small diameter of nano-scale optic fiber may enable a reduction in the cross-sectional area of the probe, which in turn may reduce the size of the surgical incision in sclera 36 of eye 20 (see FIGS. 1 and 2) though which the probe is inserted.

Figure 5:
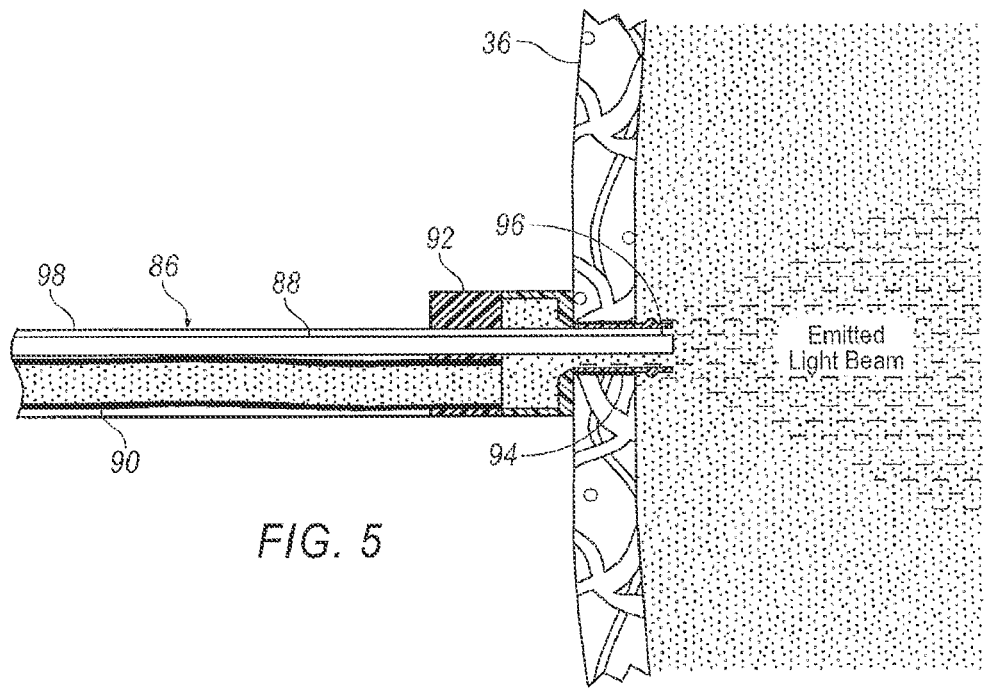
FIG. 5 is a schematic partial cross-sectional view of an exemplary integrated infusion cannula and illumination probe that may be employed with the intraocular illumination systems of FIGS. 3 and 6.

Due to the small size of nano-scale optic fibers, it may be possible to integrate illumination probe 50 with another surgical instrument, including but not limited to, infusion cannula 48 (see FIG. 2), to reduce the number of surgical incision required for inserting surgical instruments during a vitreo-retinal procedure. Some exemplary configurations of infusion cannulas employing integrated illumination optic fibers are disclosed in U.S. Pat. No. 7,783,346, which issued to Smith et al. on Aug. 24, 2010 (the "'346 Patent"). The '346 Patent is incorporated herein by reference in its entirety. Referring to FIG. 5, an exemplary configured integrated illumination probe/infusion cannula 86 may include a nano-scale fiber optic cable 88 for transmitting light emitted from laser 56 to the interior of eye 20. A hose 90 may be provided for transporting liquid or gas for delivery to the interior of eye 20. A hub 92 interconnects nano-scale fiber optic cable 88 with hose 90. A cannula 94 may be attached to hub 92. Cannula 94 provides a passage for receiving an end 96 of nano-scale fiber optic cable 88, and for delivering the fluid or gas to the interior of eye 20. Nano-scale fiber optic cable 88 and hose 90 may be enclosed in a protective sheath 98. The exemplary configuration of integrated illumination probe/infusion cannula 86 enables the two surgical instruments to simultaneously access the interior region of eye 20 through a single surgical incision. Nano-scale fiber optic cable 88 may be similarly integrated with other microsurgical instruments.

Figure 6:
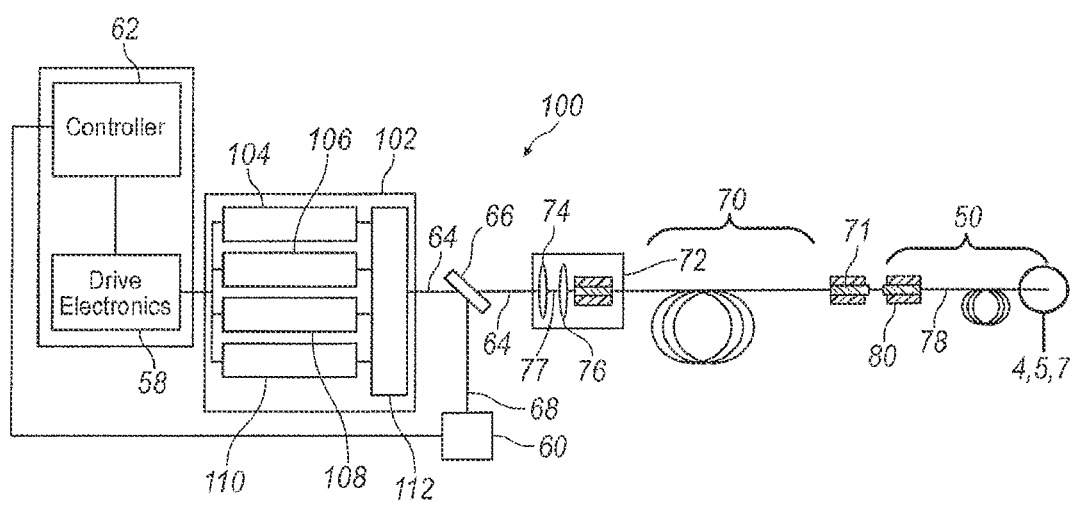
FIG. 6 is a schematic illustration of an exemplary intraocular illumination system employing multiple narrowband lasers as the light source.

With reference to FIG. 6, an endoilluminator 100 may include an alternately configured light engine 102 for generating light at a particular luminous flux and chromaticity. Light engine 102 may be similarly configured as light engine 54 (see FIG. 3), but differs by including multiple lasers for generating a generally broadband white light for illuminating an interior of eye 20. Aside from light engine 102, endoilluminator 100 is similarly configured as endoilluminator 52 illustrated in FIG. 3. Rather than employing a single laser, such as the supercontinuum laser employed with laser light source 56 (see FIG. 3), for generating a generally broadband white light, light engine 102 of endoilluminator 100 utilizes two or more lasers to produce light having selected spectral properties. In the exemplary configuration of endoilluminator 100 shown in FIG. 6, light engine 102 includes four lasers 104, 106, 108 and 110. Each laser may be configured to generate light over a different portion of the desired spectral range. A beam combiner 112 may be provided for combining the light beams emitted from the individual lasers into a single light beam 64 having a desired spectral range. Light beam 64 will have a spectral range that includes the spectral ranges of the light beams emitted from lasers 104, 106, 108 and 110. Four lasers are shown in the exemplarily configuration of endoilluminator 100, as illustrated in FIG. 3, but in practice, fewer or more lasers may be employed. The actual number of layers employed will depend at least in part on the wavelength range of the individual lasers. Generally, the broader the spectral range the fewer number of lasers that will need to be employed to produce light across a desired spectral range. Although each laser produces light over a different spectral range, it may be beneficial to have at least some overlap between the spectral ranges to help insure a uniform spectral distribution of the emitted light.

A light beam produced by combining multiple individual light beams to produce a single light beam having the spectral ranges of the individual light beams, such as implemented with light engine 102, may be subject to a phenomenon referred to as speckling. Speckling occurs when multiple light waves having different phases interfere with one another. When added together, the interferences produce a light wave having an intensity that varies randomly. Options for reducing speckling include, for example, using rotating diffusers or lenses arranged in the optical path of light beam 64 to disrupt the spatial coherence of the emitted laser light. Other options include passing the summed light beam through a vibrating or stretched coil of optic fiber, such as second dispersive element 70, to produce a uniform illumination.

Figure 7:
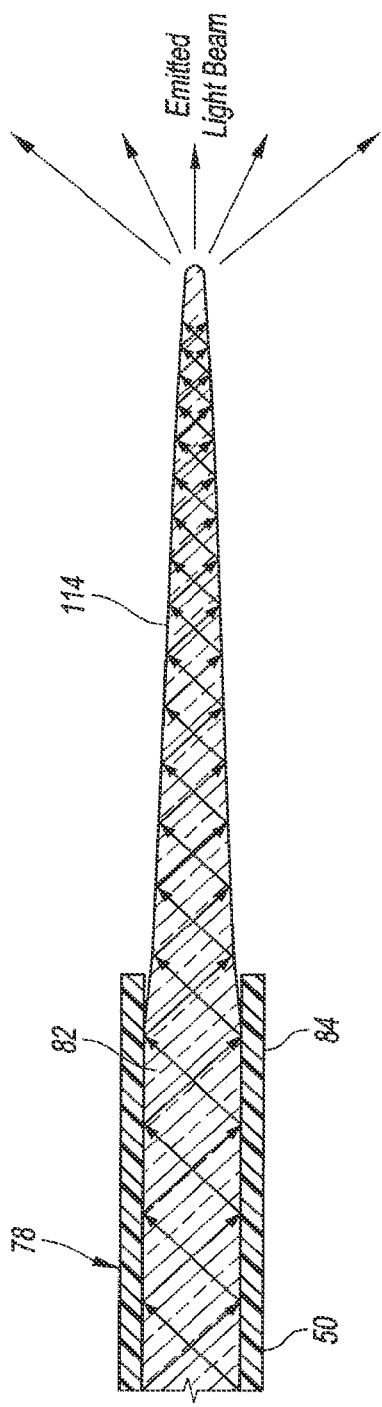
FIG. 7 is a schematic partial cross-sectional view of an exemplary illumination probe that may be employed with the intraocular illumination systems of FIGS. 3 and 6, the illumination probe including a nano-scale optical fiber having a shaped end for selectively tailoring the distribution of light emitted from the illumination probe.

It is generally desirable for light emitted from illumination probe 50 to have a relatively wide angular distribution to enable illumination of corresponding wide surgical field within eye 20. Light emitted from nano-scale optic fibers, such as may be employed with fiber optic cable 78, may have a relatively small angular distribution due to the small numerical aperture of the fiber or the small numerical aperture of the beam within the fiber. Referring to FIG. 7, one option for achieving a wider angular distribution of emitted light is to selectively taper an end 114 of fiber optic core 82. Various tapers may be employed, such as a compound parabolic concentrator, depending on the design parameters of a particular application and the angular distribution desired. Alternative methods such as adding a diffusing agent to the end of the fiber optic may be used to create a larger illumination angle.

Figure 8:
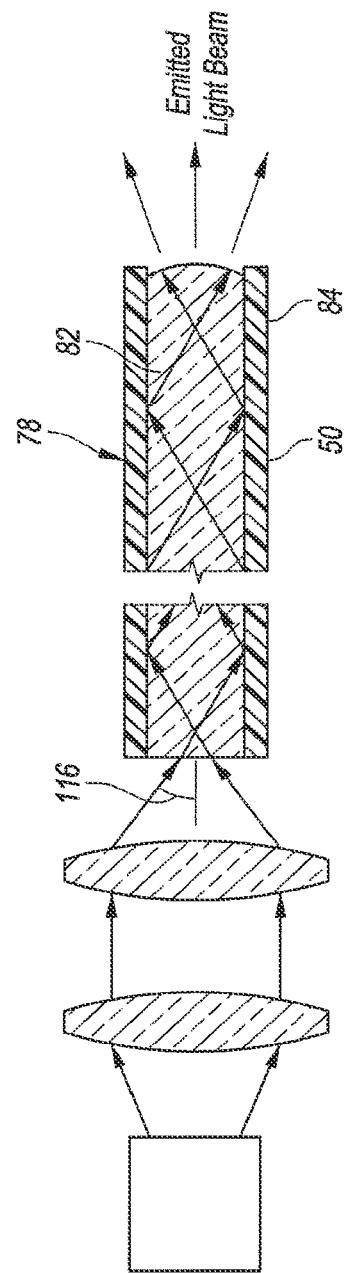
FIG. 8 is a schematic partial cross-sectional view of an exemplary illumination probe including a high numerical aperture and a nano-scale optical illumination fiber that may be employed with the intraocular illumination systems of FIGS. 3 and 6.

Referring to FIG. 8, the angular distribution of light emitted from fiber optic cable 78 may also be increased by employing a fiber optic cable having a high numerical aperture. A high numerical aperture indicates a large difference in refractive index between fiber optic core 82 and cladding 84. Fiber optic cables having large numerical apertures can generally accept light over a broader range of incident angles than fiber optic cables having smaller numerical apertures. Increasing an incidence angle 116 at which light enters fiber optic cable 78 generally results in an increase in the angular distribution of light emitted from the fiber optic cable. Increasing the numerical aperture of fiber optic cable 78, when employed in conjunction with an increased incidence angle of the light delivered to the fiber optic cable, may improve the angular distribution of light emitted from illumination probe 50.

In certain situations, photodarkening, or color centering, may occur. Photodarkening is a multiphoton process, and the probability of its occurrence is proportional to the peak power of a pulse. Accordingly, in certain embodiments, a pulse stretching element in the optical train may alleviate this condition. For example, a pulse stretching element may stretch a 100 to 200 picosecond (ps) pulse to 1 nanosecond (ns). In certain embodiments, a temporally dispersive element may also accomplish this.

It will be appreciated that the exemplary surgical illumination system described herein has broad applications. The foregoing configuration were chosen and described in order to illustrate principles of the methods and apparatuses as well as some practical applications. The preceding description enables others skilled in the art to utilize methods and apparatuses in various configurations and with various modifications as are suited to the particular use contemplated. In accordance with the provisions of the patent statutes, the principles and modes of operation of the disclosed surgical illumination system have been explained and illustrated in exemplary configurations.

It is intended that the scope of the present methods and apparatuses be defined by the following claims. However, it must be understood that the disclosed surgical illumination system may be practiced otherwise than is specifically explained and illustrated without departing from its spirit or scope.

It should be understood by those skilled in the art that various alternatives to the configuration described herein may be employed in practicing the claims without departing from the spirit and scope as defined in the following claims. The scope of the disclosed surgical illumination system should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the device and that the method and apparatus within the scope of these claims and their equivalents be covered thereby. In sum, it should be understood that the device is capable of modification and variation and is limited only by the following claims.

What is claimed is:

1. A surgical illumination system comprising:
   a first laser configured to emit a first light beam having a first spectral range;
   a second laser configured to emit a second light beam having a second spectral range;
   a beam combiner arranged in an optical path between at least one of the first and second lasers and an illumination probe, the beam combiner configured to:
   combine the first and second light beams; and
   emit a third light beam having a third spectral range that includes the first spectral range and the second spectral range; and
   the illumination probe comprising a fiber optic cable for delivering at least a portion of the third light beam to a surgical site.

2. The surgical illumination system of claim 1, wherein the fiber optic cable includes a fiber optic core having a diameter of 100 microns or less.

3. The surgical illumination system of claim 1, wherein the fiber optic cable includes a fiber optic core with a contoured end for emitting the at least a portion of the third light beam.

4. The surgical illumination system of claim 1, wherein the first spectral range extends over at least a portion of the visible spectrum.

5. The surgical illumination system of claim 1, wherein the first spectral range extends over substantially the entire visible spectrum.

6. The surgical illumination system of claim 1, wherein the first laser is a supercontinuum laser.

7. The surgical illumination system of claim 1, further comprising an optical coupler for optically connecting the third light beam to the illumination probe.

8. The surgical illumination system of claim 1, further comprising a dispersive element for selectively adjusting a time domain of the third light beam, the dispersive element arranged in an optical path between the first laser and the illumination probe.

9. The surgical illumination system of claim 1, further comprising a surgical probe integrated with the illumination probe.

10. The surgical illumination system of claim 1, wherein the first and second spectral ranges at least partially overlap.

11. A surgical illumination system comprising:
a light engine comprising:
- a first laser configured to emit a first light beam having a first spectral range;
- a second laser configured to emit a second light beam have a second spectral range; and
- a beam combiner arranged in the optical path of at least one of the first and second lasers and operable to combine the first and second light beams to generate a third light beam having a third spectral range that includes the first spectral range of the first light beam and the second spectral range of the second light beam;

an illumination probe including a fiber optic core having a diameter of 100 microns or less;
an optical coupler optically coupling the fiber optic core of the illumination probe to the light engine.

12. The surgical illumination system of claim 11, wherein at least one of the first laser and the second laser is configured as a supercontinuum laser.

13. The surgical illumination system of claim 11, further comprising at least one of a dispersion element and a despeckling element arranged an optical path between the light engine and the illumination probe.

14. The surgical illumination system of claim 11, wherein the first spectral range includes substantially the entire visible spectral range.

15. The surgical illumination system of claim 11, wherein an intensity distribution of the first beam of light is shaped to achieved a desired output pattern.

16. The surgical illumination system of claim 11, wherein the first spectral range overlaps the second spectral range.

* * * * *